United States Patent [19]

Kamen

[11] Patent Number: 4,778,451
[45] Date of Patent: Oct. 18, 1988

[54] FLOW CONTROL SYSTEM USING BOYLE'S LAW

[76] Inventor: Dean L. Kamen, 44 Gage Rd., Bedford, N.H. 03102

[21] Appl. No.: 836,023

[22] Filed: Mar. 4, 1986

[51] Int. Cl.$^4$ .............................................. F61M 5/00
[52] U.S. Cl. ..................... 604/67; 604/251; 128/DIG. 13; 73/149; 417/395
[58] Field of Search .................. 604/65, 67, 251, 253; 128/DIG. 12, DIG. 13; 73/149; 417/384–389, 395

[56] References Cited

U.S. PATENT DOCUMENTS 2,116,636  5/1938  Neumann .......................... 73/149 X
2,747,400  5/1956  Fatio ................................... 73/149
4,634,430  1/1987  Polaschegg .

FOREIGN PATENT DOCUMENTS

3408331C2  6/1986  Fed. Rep. of Germany .
8404460  11/1984  PCT Int'l Appl. .

Primary Examiner—Stephen C. Pellegrino
Attorney, Agent, or Firm—Bruce D. Sunstein; Kay H. Pierce; Paul C. Flattery

[57] ABSTRACT

A dispensing arrangement in a fluid line that isolates a region of fluid in the line from pressure effects in the line outside the region. A housing of measuring fluid surrounds the region so that changes in the measurement fluid pressure cause changes in the pressure of the original fluid in the region. Predetermined volume increments of the measurement fluid are displaced, causing changes in the original fluid pressure in the region which are measured by a pressure transducer. The dispensing arrangement also repetitively dispenses fluid into and out of the region in increments monitored by the pressure transducer.

7 Claims, 5 Drawing Sheets 4,778,451

FLOW CONTROL SYSTEM USING BOYLE'S LAW

FIELD OF INVENTION

The present invention relates to systems for controlling fluid flow, particularly from a reservoir to a patient, although other embodiments are discussed below.

BACKGROUND ART

Numerous devices exist in the prior art for controlling fluid flow for use in intravenous administration arrangements and similar applications. Many of these designs, including the design disclosed in U.S. Pat. No. 4,515,588, utilize elaborate systems for pressure regulation. The inventor is unaware, however, of any system which utilizes an external volume displacement arrangement for calibrating a dispensing arrangement that is monitored by a pressure sensitive device.

DISCLOSURE OF INVENTION

A preferred embodiment of the invention utilizes a dispensing arrangement in a fluid line that isolates a region of fluid in the line from pressure effects in the line outside the region. The dispensing arrangement also has a provision for repetitively dispensing fluid into and out of the region. A pressure transducer monitors pressure changes in the region. The system also includes a provision for housing a measurement fluid (such as air) in relation to the region in such a manner that a change in the measurement fluid pressure causes a change in the pressure of the original fluid in the region. There is also a displacement arrangement for repetitively displacing predetermined volume increments of the measurement fluid, so that these volume increments cause changes in the original fluid pressure in the region which are measured by the pressure transducer. Finally, a control arrangement causes the dispensing arrangement to dispense the original fluid in increments that are calibrated by the displacement arrangement and monitored by the pressure transducer. In a further embodiment, the control arrangement is operated so that the predetermined volume increments of measurement fluid are matched by the increments of original fluid dispensed by the dispensing arrangement.

BRIEF DESCRIPTION OF THE DRAWINGS

The foregoing objects and features of the invention are better understood with reference to the following description taken with the accompanying drawings in which.

DETAILED DESCRIPTION OF SPECIFIC EMBODIMENTS

Figure 1:
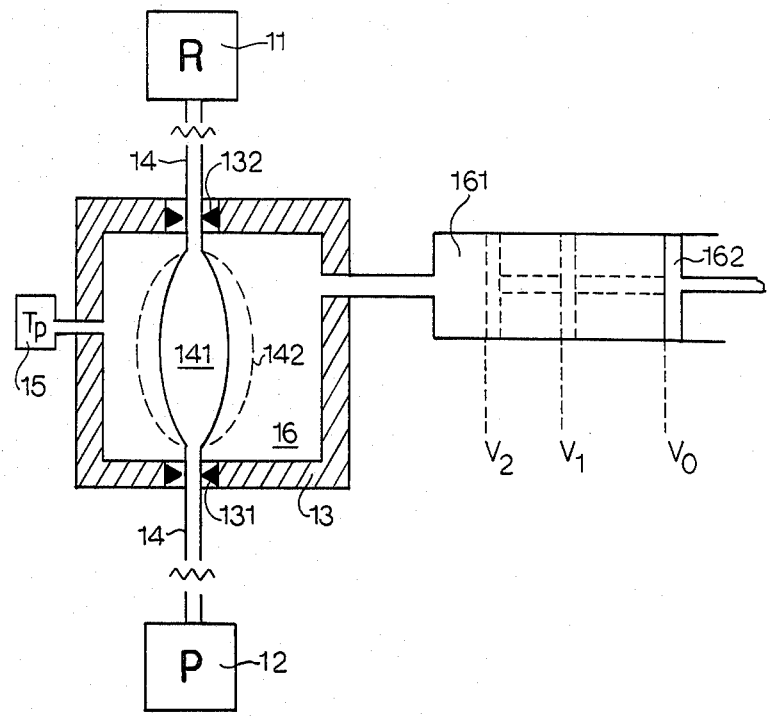
FIG. 1 is a simplified schematic of a first embodiment of the invention.

FIG. 1 illustrates a fluid control system in accordance with the present invention for controlling fluid from a reservoir 11 into a patient 12. The fluid line 14 passes through a measurement housing 13 that is substantially airtight. The measurement housing 13 is provided with an upper valve 132 and a lower valve 131 for controlling flow into and out of flexible enclosure 141 located within the measurement housing. The portion of the interior 16 of the housing not occupied by the flexible enclosure 141 is filled with air. The interior 16 of the housing 13 is in communication with a volume standard that comprises a cylinder 161 in which travels a piston 162. The air pressure within the housing 13 is monitored by pressure trandsucer 15. It can be seen that the pressure in the interior 16 of the housing is a function of the volume occupied by flexible enclosure 141 and the effective volume of the interior (16) as modified by displacement of the piston 162 within the cylinder 161.

Study of FIG. 1 will reveal that displacement of the piston by some amount, for example 1 cc, from position $V_0$ to position $V_1$ removes 1 cc from the total effective volume of the interior 16 of the measurement housing 13. As a result of Boyle's Law, there is an increase in air pressure in the interior 16 that is monitored by the pressure transducer 15. (Because the enclosure 141 is flexible, there is a concomitant increase in fluid pressure within the enclosure 141.) Let us assume that there is sufficient fluid in the enclosure 141 that it occupies the position shown in dashes as item 142. If the lower valve 131 is opened, fluid will drain from the enclosure shown as item 142 through the line 14 into the patient 12. Since valve 132 is closed, the walls of the flexible enclosure 142 will occupy a decreasing volume as the fluid leaves the enclosure, and at some point the decrease in volume occupied by the enclosure 142 will equal 1 cc. At this point, the pressure within the interior 16 of the measurement housing 13 has returned to the original pressure, since the total volume of the interior 16 that is available for occupancy by air has returned to the original volume. Thus the pressure transducer 15 can be used to determine when the original pressure has returned and can be used to establish the point in time when valve 131 should be closed in order for exactly 1 cc of fluid to have been dispensed into the patient. In this fashion, the volume standard that includes cylinder 161 and piston 162 serves as a template for determining the increment of fluid that may be dispensed through the flexible enclosure 141. The system may be restored to an initial position by retracting piston 162 to position $V_0$, and opening valve 132 until sufficient fluid flows into enclosure 141 that again the pressure indicated by transducer 15 has returned to the original level.

Figure 3:
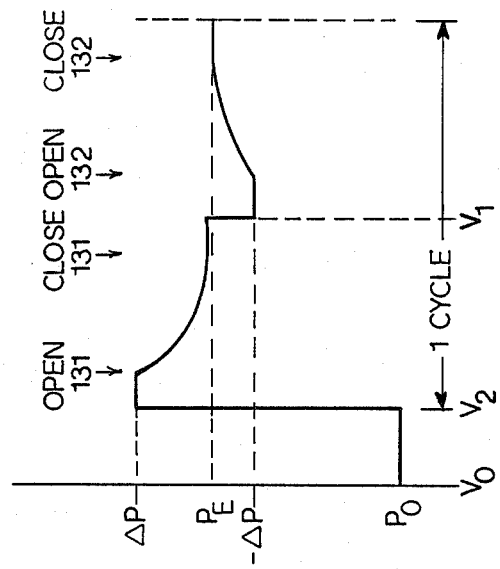
FIGS. 2–4 illustrate operation of the embodiment of FIG. 1.
Figure 2:
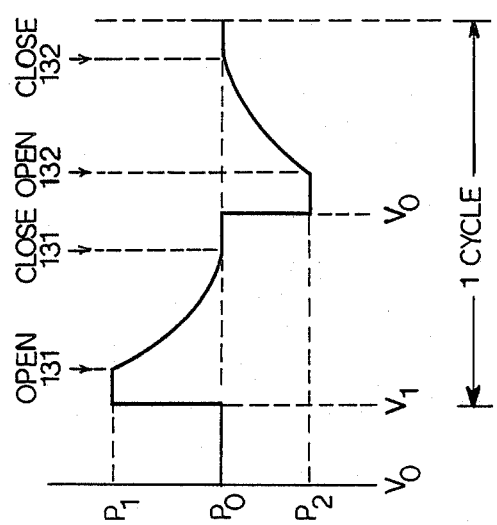
Figure 4:
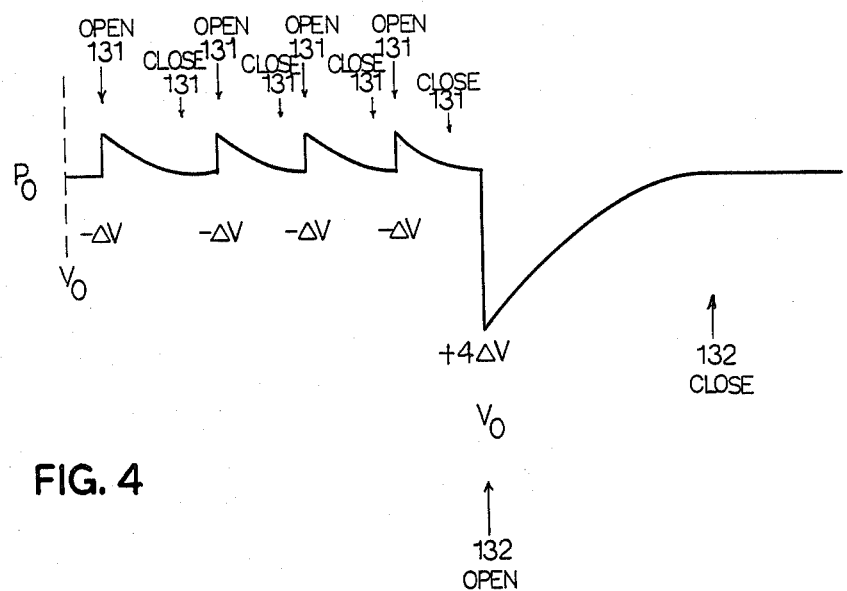

This cycle is illustrated in the graphs of FIGS. 2 through 4. In FIG. 2, atmospheric pressure is indicated by $P_0$. When the volume shrinks from $V_0$ to $V_1$ the pressure immediately rises to a new pressure $P_1$. After a desired interval, valve 131 is opened, and the pressure within the interior 16 of the measurement housing 13 is permitted to return to pressure $P_0$, at which point valve 131 is closed. Thus there has been dispensed from flexible enclosure 141 a volume increment of fluid equal to $(V_0 - V_1)$. After an additional desired interval, the piston 162 is returned to position $V_0$, at which point the pressure drops to amount $P_2$ in the interior 16. After another desired interval, the upper valve 132 is opened and the pressure is monitored until it returns to point $P_0$, whereupon valve 132 is closed and the same volume increment $(V_0 31 V_l)$ has been dispensed into flexible enclosure 141. After another desired interval, the cycle can begin again with displacement of the piston to position $V_l$ and so forth.

FIG. 3 illustrates that the same process shown in FIG. 2 may be conducted at an elevated pressure, so that the system acts in effect as a pump rather than merely a flow control device. In this embodiment atmospheric pressure indicated by $P_0$ is below the elevated operating pressure $P_E$. The piston 162 is used to displace volume from initial position $V_0$ to position $V_2$, whereupon the pressure in the interior 16 of the measurement housing 13 exceeds pressure $P_E$ by an amount $\Delta P$. When valve 131 is opened, the pressure is permitted to fall to $P_E$, and when after 131 is closed, the piston is not moved back to position $V_0$, but rather only to position $V_l$, so that pressure falls by an amount $\Delta P$ from $P_E$, but does not reach $P_0$. In this fashion pressure is maintained within a predetermined limit $\Delta P$ of the desired elevated pressure $P_E$.

In connection with FIGS. 2 and 3 it maybbe remarked that in fact the relation between pressure and volume is also a function of temperature, and that compression of the air by piston 162 would also cause a momentary increase in temperature of the air within the measurement housing 13 and that the elevated temperature could lead to errors. In this regard, it is within the domain of the present invention to monitor the temperature change and compensate the pressure system for temperature effects. However, I have conducted experiments and performed calculations that indicate that relatively high accuracy (measurement of volume within a percent or so) can be achieved without temperature compensation. It should also be noted that points $P_l$ and $P_2$ are somewhat arbitrary, and that, therefore, as long as the pressure transducer has errors in accuracy that are reproducible, the system will avoid errors introduced by the pressure transducer in any form, and the accuracy of the system will tend to be limited by the reproducibility of the volume displacements caused by piston 162.

FIG. 4 illustrates another mode of operation of the system. In this mode, the piston 162 is repeatedly displaced to the left in small increments $\Delta V$. Each time the resulting pressure increase from $P_0$ is thereafter cancelled out by opening valve 131 until the pressure returns to $P_0$, whereupon valve 131 is closed. In this fashion, an amount of fluid V is dispensed each time through the fluid line. At some point after the piston has fully traversed its stroke to the left, valve 131 is closed for the last time, the piston is moved to the right, returning the system to volume $V_0$, at which point the upper valve 132 is opened, the flexible enclosure 141 is refilled, and upper valve 132 is closed when pressure again returns to $P_0$. Numerous other configurations are possible, the point being only that the piston 162 and cylinder 161 permit calibration of the dispensing system, the pressure of which can be monitored by a pressure transducer 15. Although the illustration has been made using air as the measurement fluid in the interior 16 of the measurement housing 13, other fluids, including other gases and other liquids, may also be feasibly utilized. It should also be noted that the pressure transducer produces more information than simply departures from equalibrium pressure $P_0$ or $P_E$. In particular, the slope of the curve in these figures may also be monitored, thereby providing an extremely accurate sytem for determining on an instantaneous basis the flow rate. In fact, flow rate can be monitored so that a sudden decrease from a statistically determined average flow rate (i.e., slope of the pressure versus time curve) for a given patient can be used for causing the system to enter an alarm state indicating, for example, that the needle is no longer in the vein. That is, a sudden decrease in the rate of change of pressure with time during the flow portion of the cycle may be used as an indication of infiltration. The horizontal portions of the curves in FIG. 2 and 3 may also be used to monitor the system for air leaks and related phenomena; that is, the elevated or depressed pressures will not remain constant in the presence of such leaks.

The arrangement described above also permits detecting the presence of air in the fluid line. Under such circumstances, the pressure change when the volume is changed by piston 162 will be smaller than in the case when fluid is properly flowing. For example, with respect to FIG. 2, in the presence of air within the flexible enclosure 141, the usual threshhold $P_l$ will not be reached when the volume changes to $V_l$. The failure to achieve the normal pressure differential can be viewed as an alarm state. However, since the valve arrangement 131 and 132 is quite flexible, before entering the alarm state, valve 131 may be retained in its closed position and the piston 162 could be displaced maximally to the left to cause a great increase in pressure in the interior 16 of the measurement housing 13 with valve 132 open, so as to cause enclosure 141 to shrink to minimum volume; thereafter, piston 162 can be moved back to the right and flexible enclosure 141 be permitted to expand again and the test repeated to see if the normal rise in pressure has occurred. If it has not occurred a second time, then the alarm state would be entered. Otherwise, the approach just described is a reasonable method of purging the enclosure 141 from minor air bubbles. All of this has been done without risk of harm to the patient, since valve 131 has remained closed.

Although the system has been described as appropriate for controlling flow from a reservoir into a patient, this system may also be used for monitoring fluid flow out from a patient, for example in the measurement of urine volume. In such an embodiment, item 11 would constitute the catheter or other connection to the patient and item 12 of FIG. 1 would constitute a reservoir. Valve 131 would be closed while valve 132 could be opened. Periodically, valve 132 would be closed and then a measurement cycle such as illustrated in FIG. 2 would be performed to dispense a determined amount of fluid from the enclosure 141.

It should be noted that FIG. 1 also provides a simple arrangement for measuring the blood pressure of the patient. In this arrangement, the upper valve 132 is closed, and lower valve 131 is opened and the system is permitted to reach equilibrium. In this fashion, the pressure in line 14 is indicative of the patient's blood pressure, which may be monitored by pressure transducer 15.

Figure 5:
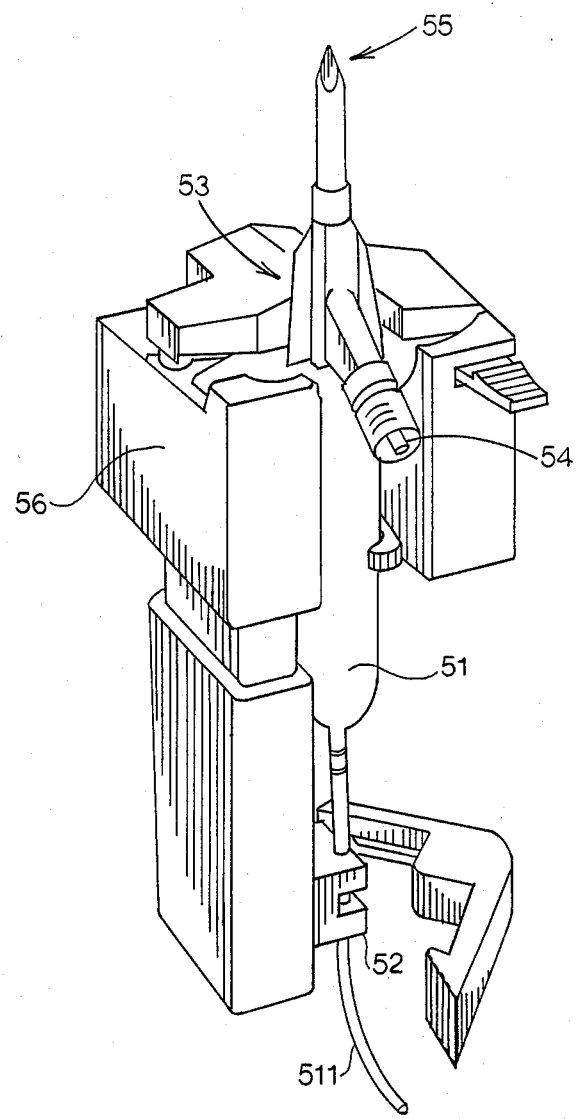
FIGS. 5 and 6 show different perspective views of a second embodiment of the invention.

Although the invention has been described thus far with a separate measurement housing 13, such a housing may be combined with a drip chamber, as illustrated in FIG. 5. In FIG. 5 one may see a drip chamber 51 including a spike end 55, a fluid line end 511 that is held in a case 56. The drip chamber is provided with a fitting 54 for attachment both to a pressure transducer such as indicated by item 15 in FIG. 1 and to a volume standard including a piston 162 and cylinder 161 such as illustrated in FIG. 1. The volume standard can cause changes in the air pressure within the drip chamber 51 in the same fashion discussed above in connection with FIG. 1, except that the pressure changes are directly transmitted to the fluid, rather than through the intermediary of the flexible enclosure 141. The case 56 is provided with a valve in the lower region 52 of the drip chamber and another valve in the upper region 53 of the drip chamber. The valve in region 52 can be a normal crimp type valve operative on the fluid line. The upper valve 52 may be any suitable valve, although one is described in further detail in connection with FIGS. 6 and 7.

Figure 6:
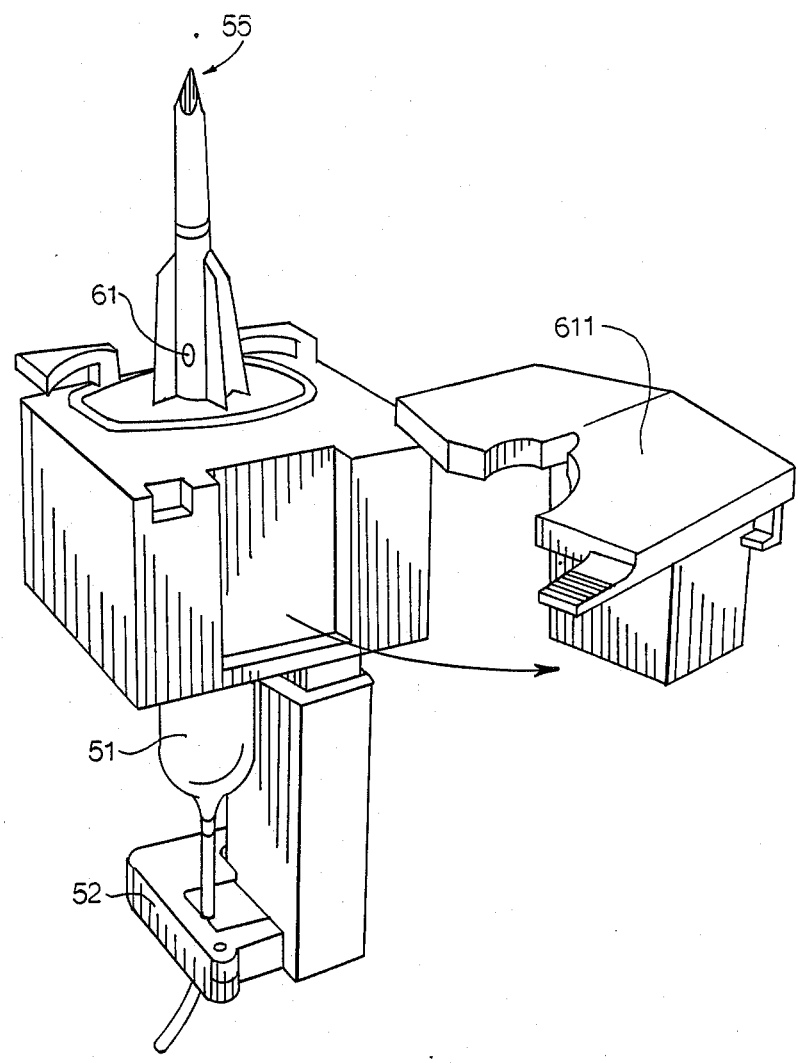

FIG. 6 presents another view of the system of FIG. 5. The drip chamber 51 in the spike end 55 is provided with a hole 61. The hole 61 is in the external rigid plastic portion of the drip chamber and would reach directly into the fluid line, except that the interior of the spike portion 55 is fitted with a piece of silicon rubber tubing, the outside walls of which engage tightly within the inside walls of the spike. Thus, hole 61 provides direct access to the outer wall of the silicon tubing but is outside the fluid flow path from the tip of spike 55 into the drip chamber 51. The upper valve acctuator housing 611, however, contains an actuator pin which is capable of moving into and out of the hole 61 in such fashion as to squeeze the silicon tubing when the pin is in the closed position. In this fashion flow through the spike 55 is halted when the pin is in the closed position. When the pin is in the open position, flow is permitted through spike 55. In this embodiment the silicon tubing, the hole 61, and the pin in upper valve actuator housing 611 provide an upper valve.

Figure 7:
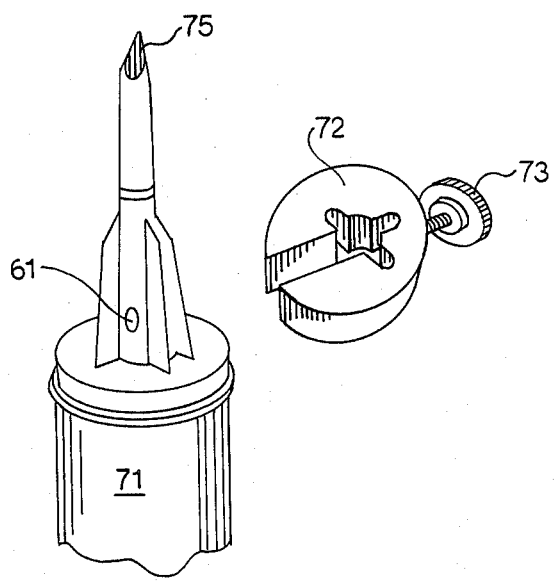
FIG. 7 shows a detailed drawing of a drip chamber for use in the embodiment of FIGS. 5 and 6.

As illustrated in FIG. 7, the upper valve access hole 61 may be provided with a manual adjustment in lieu of the automatic system described in connection with the previous figures. In the manual adjustment embodiment, adjustment ring 72 may be inserted over the spike end 75 until the thumb screw 73 can be turned to cause the inside portion of the screw to enter hole 61 and compress the silicon tube inside the spike 75. The degree of compression of the tube will regulate the flow through the spike 75. When the manual adjustment ring assembly 73 is removed from the spike, it may be used in the system of FIGS. 5 and 6.

Figure 8:
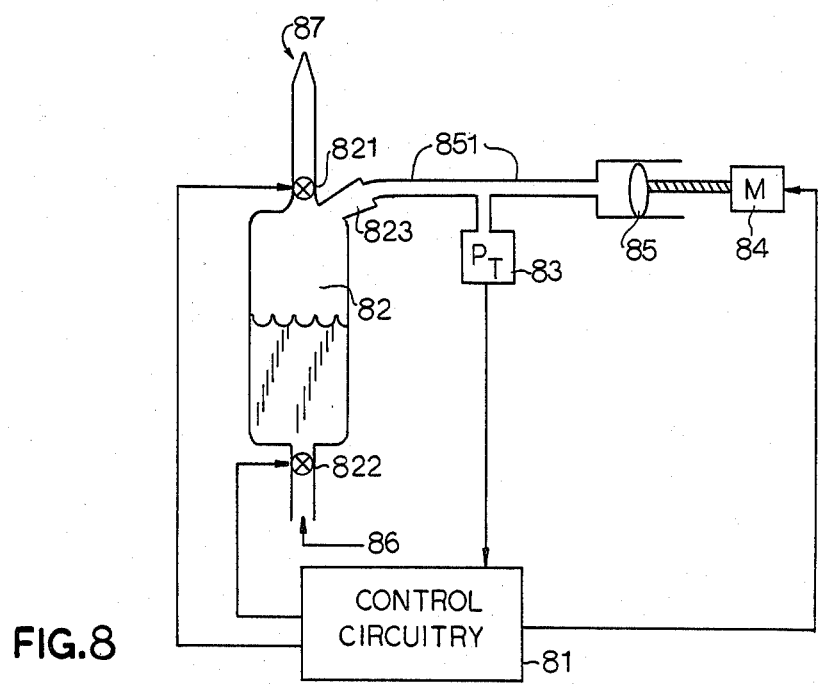
FIG. 8 shows a schematic diagram of the system illustrated in FIGS. 5 and 6.

The system of FIGS. 5 and 6 is illustrated schematically in FIG. 8, where there is shown the drip chamber 82 having spike end 87, upper valve 821, and lower valve 822, which valves are operated by control circuitry 81. A piston arrangement 85 compresses air in line 851, which is connected at fitting 823 into the drip chamber 82. Pressure in the interior of the drip chamber 82 is monitored by transducer 83, which is also connected to control circuitry 81. Motor 84 drives piston 85 in any of a variety methods well known in the art. The motor 84, which is also connected to control circuitry 81, may, for example, be a stepper motor which drives the piston by a conventional rack and pinion arrangement. In this fashion the control circuitry 81 will always know the relative position of the piston 85. Alternative sensing arrangements may utilize a simpler motor with Hall effect devices, for example, to monitor position of the rack. The cycles of operation of this system are identical to those as discussed above in connection with FIG. 1.

It should be noted that the embodiments of FIG. 1 and FIG. 8 can be used to determine the volume of fluid in the flexible enclosure 141 and the drip chamber 82 by a related but somewhat different technique. In particular one may cause a slight perturbation in volume by the piston 162 or 85. If the resulting increase in pressure is measured by the pressure transducer 15 or 83, Boyle's Law may be used directly in order to determine the volume of fluid in the drip chamber or the flexible enclosure. This approach could be used to determine the volume of fluid in any flexible enclosure in the case of FIG. 1 or in any rigid enclosure in the case of FIG. 8.

I claim:

1. A system for controlling flow of a first fluid in a line, the system comprising:
    dispensing means (i) for isolating a region of the first fluid in the line from effects of pressure in the line outside of the region, such region having an input and an output for the first fluid, and (ii) for repetitively dispensing into and out of the region increments of first fluid, whereby such dispensing may cause changes in pressure of the first fluid in the region;
    pressure measurement means for measuring changes in pressure of the first fluid in the region;
    measurement fluid housing means for housing a measurement fluid in relation to the region such that a change in the measurement fluid pressure causes a change in the first fluid pressure in the region;
    displacement means for repetitively displacing predetermined volume increments of measurement fluid, whereby the resulting changes in first fluid pressure are measured by the pressure measurement means;
    control means, in communication with the pressure measurement means, the displacement means, and the dispensing means, for causing the dispensing means to dispense first fluid in increments that are calibrated by the displacement means and monitored by the pressure measurement means.

2. A system according to claim 1, wherein (i) the dispensing means includes an input valve at the first fluid input to the region and an output valve at the first fluid output from the region and (ii) the measurement fluid is air.

3. A system according to claim 2, wherein the measurement fluid housing means includes a drip chamber through which the first fluid flows and the upper region of which is in communication with the displacement means.

4. A system according to claim 2, (i) wherein the measurement fluid housing means includes a substantially airtight housing around the region, such housing in communication with the displacement means, and (ii) further comprising a flexible enclosure, within the housing, for containing the first fluid in the region.

5. A system according to claim 3, wherein the control means includes means for causing the dispensing means to dispense first fluid in the same increments of volume as displaced by the displacement means.

6. A system according to claim 4, wherein the control means includes means for causing the dispensing means to dispense first fluid in the same increments of volume as displaced by the displacement means.

7. A system according to claim 5, wherein the control means includes means for causing the first fluid in the region to have an average line pressure regulated at a desired amount lying in the range of ½ to 10 lbs. per square inch.

* * * * *